United States Patent
Lu et al.

(10) Patent No.: US 7,985,857 B2
(45) Date of Patent: Jul. 26, 2011

(54) USAGE OF POLY-3-HYDROXYBUTYRATES IN PREPARATION OF β-LACTAM COMPOUNDS

(75) Inventors: Weichuan Lu, Tianjin (CN); Qian Zhang, Tianjin (CN); Xin Cheng, Nianjin (CN)

(73) Assignee: Tianjin Greenbio Material Co. Ltd., Teda, Tianjin (CN)

( * ) Notice: Subject to any disclaimer, the term of this patent is extended or adjusted under 35 U.S.C. 154(b) by 361 days.

(21) Appl. No.: 12/280,781

(22) PCT Filed: Oct. 16, 2006

(86) PCT No.: PCT/CN2006/002707
§ 371 (c)(1),
(2), (4) Date: Aug. 26, 2008

(87) PCT Pub. No.: WO2007/098651
PCT Pub. Date: Sep. 7, 2007

(65) Prior Publication Data
US 2009/0088566 A1    Apr. 2, 2009

(30) Foreign Application Priority Data
Feb. 28, 2006 (CN) .......................... 2006 1 0013223

(51) Int. Cl.
*C07D 205/08* (2006.01)
*C07F 7/18* (2006.01)

(52) U.S. Cl. .................. 540/357; 556/436; 556/437

(58) Field of Classification Search ............ 540/357
See application file for complete search history.

(56) References Cited

U.S. PATENT DOCUMENTS
4,791,198 A * 12/1988 Ohashi et al. ............ 540/354
* cited by examiner

*Primary Examiner* — Mark Berch
(74) *Attorney, Agent, or Firm* — Global IP Services; Tianhua Gu

(57) ABSTRACT

A method for preparing compounds having the formula(I) by using P(3HB),

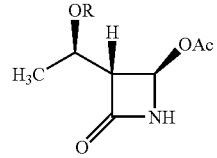
(I)

wherein R is

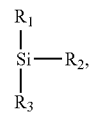

$R_1$, $R_2$, $R_3$ are lower linear or branched $C_1$-$C_4$ alkyl, comprising the steps of:
a: obtaining (3R)-3-RO—CH($CH_3$)$CH_2$COOCH$_3$ by pyrolysis of P(3HB) and protection; b: obtaining (3R)-3-RO—CH($CH_3$)$CH_2$CHO by reduction of (3R)-3-RO—CH($CH_3$)$CH_2$COOCH$_3$ ; c: enolizing (3R)-3-RO—CH($CH_3$)$CH_2$CHO and then reacting with chlorosulfonyl isocyanate, at last getting the final product by reduction; wherein (3R)-3-RO—CH($CH_3$)$CH_2$CHO is enolized by reacting (3R)-3-RO—CH($CH_3$)$CH_2$CHO with isopropenyl acetate and p-toluenesulfonic acid by heating under reflux.

3 Claims, No Drawings

USAGE OF POLY-3-HYDROXYBUTYRATES IN PREPARATION OF β-LACTAM COMPOUNDS

FIELDS OF THE INVENTION

This invention relates to the preparation of β-lactam compounds. More particularly, the usage of Poly-3-hydroxybutyrates P (3HB) in the preparation of β-lactam compounds of formula (I) is disclosed:

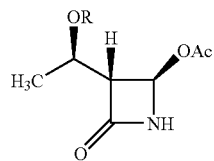

wherein:
R is

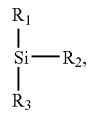

$R_1$, $R_2$, $R_3$ are lower linear or branched $C_1$-$C_4$ alkyl.

BACKGROUND OF THE INVENTION

β-lactam Compounds of Formula (I)

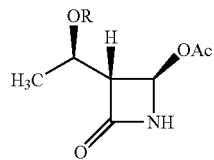

wherein:
R is

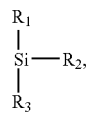

$R_1$, $R_2$, $R_3$ are lower linear or branched $C_1$-$C_4$ alkyl and important intermediates in the preparation of carbapenems (Andrew H. Berks, "Tetrahydron", Vol. 52, Page 331, 1996). So far, there have been a large number of methods to synthesize aforesaid compounds, such as, using 6-aminopenicillanic acid as the starting material (Yoshida, A.; Hayashi, T.; Takeda, N.; Oida, S.; Ohki, E. *Chem. Pharm. Bull.* 1981, 29, 2899-2909); using threonine (Shiozaki, M.; Ishida, N.; Maruyama, H.; Hiraoka, T. *Tetrahedron* 1983, 39, 2399-2407) as the starting material; using (3R)-3-hydroxybutyrate (Ohashi, T.; Kan, K.; Ueyama, N.; Sada, I.; Miyama, A.; Watanabe, K. U.S. Pat. No. 4,861,877, Aug. 29, 1989) as the starting material and so on. However, the procedures using the above-mentioned starting material either cause pollution by the usage of heavy metal compounds, like mercury acetate and lead tetraacetate; or increase the cost by the usage of excessive silicon reagents, Chiral material and catalyst.

Therefore, there is a persistent need for a skilled person in the art to seek for a suitable starting material and to optimize the synthesis process, so as to cut the use of the high cost reagents and to reduce pollution.

SUMMARY OF THE INVENTION

Through a great deal of experiments, the inventors of this invention have discovered poly-3-hydroxybutyrate as the starting material for the preparation of compound of formula (I)

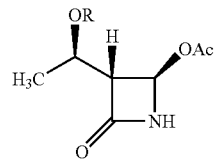

, and developed procedures suitable for production of synthesizing abovementioned compounds on large scale as well, which comprises, obtaining substituted (3R)-3-hydroxybutyrateane acid methyl ester from P(3HB), getting substituted (3R)-3-hydroxy butyraldehyde by reduction, after enolization and reacting with chlorosulfonyl isocyanate to obtain the compound of formula (I), wherein R is

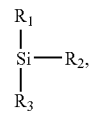

$R_1$, $R_2$, $R_3$ are lower linear or branched $C_1$-$C_4$ alkyl. The new method, which has routines as follows:

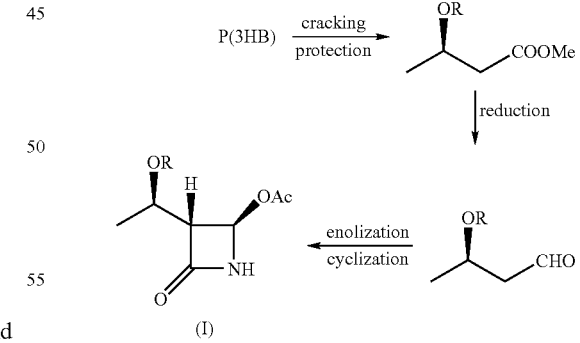

wherein R is

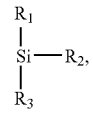

$R_1$, $R_2$, $R_3$ are lower linear or branched $C_1$-$C_4$ alkyl, has less steps and higher yields compared with the previous ones. Meanwhile, environment polluting reagents and high cost reagents are not used in the method, whereby the total cost is reduced and pollution is alleviated.

More specifically, the present invention discloses that:

1, The usage of P(3HB) in the preparation of compounds of formula (I):

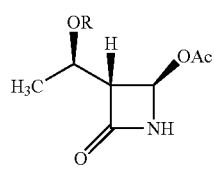

wherein R is

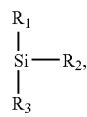

$R_1$, $R_2$, $R_3$ are lower linear or branched $C_1$-$C_4$ alkyl.

2, The usage according to item 1, wherein R is selected from 1-t-butyl-dimethysilyl, isopropyl-dimethysilyl and triisopropylsilyl.

3, A method of preparing compounds having the formula (I) as defined above by using P(3HB), comprises:
   a: obtaining (3R)-3-RO—CH(CH$_3$)CH$_2$COOCH$_3$ by decomposition of P(3HB) and protection;
   b: obtaining (3R)-3-RO—CH(CH$_3$)CH$_2$CHO by reduction of (3R)-3-RO—CH(CH$_3$)CH$_2$COOCH$_3$;
   c: enolizing (3R)-3-RO—CH(CH$_3$)CH$_2$CHO, and then reacting with chlorosulfonyl isocyanate, at last getting the final product by reduction.

4, The method according to item 3, wherein the step a is: refluxing P(3HB) with absolute methanol and sulphuric acid, post-processing to obtain initial product, then reacting with substitutional methylsilyl chloride.

5, The method according to item 4, wherein the reflux lasts for 3 days.

6, The method according to item 3, wherein (3R)-3-RO—CH(CH$_3$)CH$_2$COOCH$_3$ is (3R)-3-t-butyl-dimethylsiloxy methyl butyrate.

7, The method according to item 3, wherein the enolization procedure in the step c is reacting (3R)-3-RO—CH(CH$_3$)CH$_2$CHO with isopropenyl acetate and p-toluenesulfonic acid by heating refluxing.

8, The method according to item 3, wherein the reducing agent used in the step c is sodium bisulfite.

Poly-3-hydroxybutyrates P(3HB) as the starting material used in the present invention is a kind of thermoplastic resins, with favorable biodegradability and biocompatibility, and is mainly used as a biodegradable material. In the present invention, compared with synthesizing substituted (3R)-3-RO—CH(CH$_3$)CH$_2$COOCH$_3$ with (3R)-3-hydroxymethylbutyrate, it is very convenient to obtain P(3HB) as the starting material with a lower price for preparation of β-lactam compounds having formula (I), to synthesize (3R)-3-RO—CH(CH$_3$)CH$_2$COOCH$_3$, wherein the 3-hydroxy group is substituted by RO. Furthermore, the condition of the reaction is to reflux P(3HB) with methanol and sulphuric acid, post-processing to obtain initial product, then reacting with substitutional methylsilyl chloride to obtain (3R)-3-RO—CH(CH$_3$)CH$_2$COOCH$_3$.

(3R)-3-RO—CH(CH$_3$)CH$_2$CHO can be synthesized from (3R)-3-RO—CH(CH$_3$)CH$_2$COOCH$_3$ started by P(3HB) with traditional reactions, for example, react with iBu2AlH under low temperature, then the mixture is poured into saturated potassium sodium tartrate solution, ether is added, after that the mixture is extracted, dried, evaporated to dryness, finally subjected to silica gel column for purification.

The enolate obtained from enolization of (3R)-3-RO—CH(CH$_3$)CH$_2$CHO is subjected with chlorosulfonyl isocyanate, reduced by gentle reducing agent sodium bisulfite, purified on silica gel column to yield final product with 99% ee.

PREFERRED EMBODIMENTS

The following examples are meant to illustrate the present invention in detail, and should not be known as the limitation of it in any way. The yields are molar yields, the reagents are commercial chemical pure reagents, unless stated otherwise, the solvents of all the solutions are water if not mentioned specially.

P(3HB) a product is from Tianjin Green Biosciences Limited Company Polarimeter model: WZZ-1, Shanghai Precision Instruments Co., Ltd. NMR spectrometer model: Bruker AVANCE DRx-500, Bruker Optics Melting point instrument model: WRS-2A, Shanghai Precision Instruments Co., Ltd.

EXAMPLE 1

Preparation of (3R)-3-t-butyl-dimethylsiloxymethyl butyrate 80 g P(3HB) is dissolved in 1 L absolute dichloroethane. The mixture is at reflux for 1 h, 20 ml concentrated sulfuric acid and 400 ml absolute methanol are added, the whole is at reflux for three more days and then cooled to room temperature. 200 ml saturated NaCl solution is added to the reaction mixture, then the whole is stirred for 30 minutes. The aqueous phase is separated, washed for three times with 500 ml chloroform in total. The combined organic layers are washed for three times with 200 ml saturated NaCl solution\200 ml saturated sodium bicarbonate solution and 200 ml saturated NaCl solution respectively. Dried over magnesium sulfate, the mixture is evaporated under reduced pressure to remove the solvent. The residue is subjected to reduced pressure distillation. The fractions of 61-62 centi-degree/18 mHg are collected to get 104 g product. That product is added into a three-necked flask, 400 ml dichloroethane and 50 g imidazole are added, the whole is stirred uniformly. Then 120 g 3-t-butyl-dimethyl methylsilyl chloride is added slowly into the mixture, 5 hours later, filtration is carried out. The filtrate is washed with saturated sodium bicarbonate solution HCl and saturated NaCl solution respectively. The organic layer is separated and dried over magnesium sulfate for the whole night, concentrated under reduced pressure to obtain 200 g (3R)-3-t-butyl-dimethylsiloxy methyl butyrate with yield 92.5%.

EXAMPLE 2

The Preparation of (3R)-triisopropylsiloxymethyl butyrate

The procedure is the same as that in example 1, replacing 3-t-butyl-dimethyl methylsilyl chloride with triisopropyl methylsilyl chloride to obtain 200 g (3R)-triisopropylsiloxymethyl butyrate with yield 87.2%.

EXAMPLE 3

The Preparation of (3R)-3-t-butyl-dimethylsiloxy butyraldehyde 46.4 g (3R)-3-t-butyl-dimethylsiloxymethyl butyrate is dissolved in 200 ml N-hexane, cooled to −78° C., 240 ml solution of 1 mol/L iBu$_2$AlH in N-hexane is slowly added dropwise. After the addition, the reaction mixture is kept under the same temperature to react for 2 hours. After reaction is completed, the temperature is raised slowly, and then the mixture is poured into 1 L saturated potassium sodium tartrate solution, then 1.5 L ether and 0.5 L water are added, the whole is stirred vigorously for 1 hour. After the separation, the organic phase is washed with saturated NaCl solution, the aqueous phase is washed three times with 1.2 L ether in total, the resulting organic phases are combined, dried over sodium sulfate for the whole night and evaporated under reduced pressure to remove the solvent. The resulting crude product is purified on silica gel column chromatography (the eluent: ethyl acetate:hexane=1:1), and 39.7 g (3R)-3-t-butyl-dimethylsiloxy butyraldehyde with yield 98.3% is obtained.

EXAMPLE 4

The Preparation of (3R)-triisopropylsiloxy butyraldehyde

The procedure is the same as that in example 3, replacing (3R)-3-t-butyl-dimethylsiloxy methyl butyrate with (3R)-triisopropylsiloxymethyl butyrate with amount of 54.8 g, to obtain 44 g (3R)-triisopropylsiloxy butyraldehyde with yield 90.2%.

EXAMPLE 5

The Preparation of 3R,4R)-4-acetoxy-3-[(R)-1-t-butyl-dimethyl methylsilyloxylethyl]-azetidine-2-one 20.2 g (3R)-3-t-butyl-dimethylsiloxy butyraldehyde, 15 g isopropenyl acetate and 1 g p-toluenesulfonic acid are heated at reflux, the mixture is subjected to Vigreux Column, so as to remove acetone generated in the system completely. The residual liquid is neutralized with saturated sodium bicarbonate solution until the pH value is neutrality, then the whole is evaporated under reduced pressure to remove the azeotropic mixture of water and raw material, to obtain 17.2 g enolization product with yield 70.5%.

4.90 g above-mentioned crude product is dissolved in 25 ml dichloromethane, cooled to 0° C. in ice bath, 3.40 g chlorosulfonyl isocyanate is added slowly, the system temperature is maintained below 0° C. After the whole reacts for 2 h, a reddish brown reaction mixture is obtained, then is cooled to −40° C. The cooled solution is slowly added dropwise into vigorously stirred 200 ml 0° C. saturated sodium sulfite solution; the whole is neutralized with saturated sodium hydroxide solution until pH is 8-10. The reaction procedure is monitored by Thin-layer Chromatography. When the raw material is completely reacted, the organic phase is separated, dried over magnesium sulfate over night, evaporated under reduced pressure to remove the solvent, and purified on silica gel column chromatography (the eluent: ethyl acetate:hexane=1:10), to obtain (3R,4R)-4-acetoxy-3-[(R)-1-t-butyl-dimethyl-methyl-silyloxylethyl]-azetidine-2-one, which is recrystallized in N-hexane to obtain 3.40 g white acicular crystal with yield 59.0%. Such white acicular crystal is the final product. This process includes three steps in total, with an overall yield 37.8%.

Optical rotation of the product: 53-57° (c=0.5, CHCl$_3$)
NMR (500 MHz, CDCl$_3$)
δ(ppm): 0.08 (6H, s), 0.84 (9H, s), 1.20 (3H, d), 2.01 (3H, s), 3.04 (1H, dd), 4.12 (1H, m), 5.76 (1H, d), 6.73 (NH)
Melting point: 106-110° C.

EXAMPLE 6

The Preparation of (3R,4R)-4-acetoxy-3-[(R)-triisopropylsiloxylethyl]-azetidine-2-one The procedure is the same as that in example 5, replacing (3R)-3-t-butyl-dimethylsiloxy butyraldehyde with 24.4 g (3R)-triisopropylsiloxy butyraldehyde, to obtain 10.9 g final product, with yield 33.1%.

The melting point, optical rotation and NMR data of the final product in the present invention are in accordance with those of the products disclosed in Chinese Patent publication number 85105097.

What is claimed is:

1. A method for preparing compounds of formula (I) by using P(3HB)

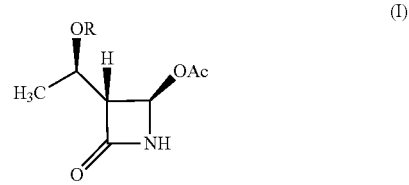

(I)

wherein R is

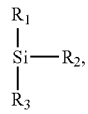

$R_1$, $R_2$, $R_3$ are lower linear or branched $C_1$-$C_4$ alkyl comprising following steps:
 a: obtaining (3R)-3-RO—CH(CH$_3$)CH$_2$COOCH$_3$ by pyrolysis of the P(3HB) and protection;
 b: obtaining (3R)-3-RO—CH(CH$_3$)CH$_2$CHO by reduction of the (3R)-3-RO—CH(CH$_3$)CH$_2$COOCH$_3$;
 c: enolizing the (3R)-3-RO—CH(CH$_3$)CH$_2$CHO and then reacting with chlorosulfonyl isocyanate, at last getting a final product of the compounds of formula (I) by reduction; wherein (3R)-3-RO CH(CH$_3$)CH$_2$CHO is enolized by reacting (3R)-3-RO CH(CH$_3$)CH$_2$CHO with isopropenyl acetate and p-toluenesulfonic acid by heating under reflux.

2. The method according to claim 1, wherein R is selected from 1-t-butyl-dimethysilyl, isopropyl-dimethysilyl and tri-isopropylsilyl.

3. The method according to claim 1, wherein (3R)-3-RO—CH(CH$_3$)CH$_2$COOCH$_3$ is (3R)-3-t-butyl-dimethylsiloxy methyl butyrate.

* * * * *